US006739179B2

United States Patent
Vogel et al.

(10) Patent No.: US 6,739,179 B2
(45) Date of Patent: May 25, 2004

(54) DEVICE FOR MEASURING THE OXYGEN CONCENTRATION IN GASES

(75) Inventors: Albrecht Vogel, Stutensee (DE); Dieter Binz, Hirschberg (DE); Manfred Wetzko, Wilhelmsfeld (DE); Peter Krippner, Karlsruhe (DE)

(73) Assignee: ABB Patent GmbH, Ladenburg (DE)

( * ) Notice: Subject to any disclaimer, the term of this patent is extended or adjusted under 35 U.S.C. 154(b) by 0 days.

(21) Appl. No.: 10/012,160

(22) Filed: Oct. 29, 2001

(65) Prior Publication Data

US 2002/0075007 A1 Jun. 20, 2002

(30) Foreign Application Priority Data

Oct. 27, 2000 (DE) .......................................... 100 53 314

(51) Int. Cl.[7] .............................................. G01N 27/62
(52) U.S. Cl. ...................... 73/25.02; 324/201; 324/204
(58) Field of Search ............................. 73/24.01, 25.02; 324/201, 204

(56) References Cited

U.S. PATENT DOCUMENTS

| 2,416,344 A | * | 2/1947 | Pauling ...................... 324/204 |
| 2,666,893 A | * | 1/1954 | Munday ..................... 324/201 |
| 2,744,234 A | * | 5/1956 | Munday et al. ............. 324/204 |
| 2,962,656 A | * | 11/1960 | Munday ..................... 324/201 |
| 3,504,275 A | * | 3/1970 | Eller et al. .................. 324/204 |
| 3,826,974 A | * | 7/1974 | Kocache et al. ............. 324/201 |
| 4,988,946 A | * | 1/1991 | Kocache et al. ............. 324/204 |
| 5,369,980 A | * | 12/1994 | Kocache ..................... 73/25.02 |
| 5,493,215 A | * | 2/1996 | Otten ......................... 324/204 |
| 6,246,227 B1 | * | 6/2001 | Hobby et al. ............... 324/204 |

FOREIGN PATENT DOCUMENTS

| DE | 2 339 960 | 3/1974 |
| DE | 198 41 723 A1 | 3/2000 |
| EP | 0 926 490 A2 | 6/1999 |
| WO | 98/125553 | 3/1998 |

* cited by examiner

Primary Examiner—Daniel S. Larkin
(74) Attorney, Agent, or Firm—Laurence A. Greenberg; Werner H. Stemer; Gregory L. Mayback

(57) ABSTRACT

A measuring device for determining the oxygen content in gases is described. The measuring device is disposed between two magnets that are positioned at a distance from one another. The measuring device is equipped with a sensor that is held rotatably within a frame. The sensor has two parallelepipedic bodies that are both made hollow or solid and are connected to one another via a web-shaped structural element. The web-shaped structural element is fastened to the frame via at least one holding element, so that the sensor can be rotated about its center of gravity. The amount of rotation is dependent on the quantity of oxygen that is concentrated between the two magnets. A current can be conducted through a conductor track led on the surface of the sensor and generates a correspondingly high restoring force by which the sensor is brought into the position of rest again.

14 Claims, 3 Drawing Sheets

DEVICE FOR MEASURING THE OXYGEN CONCENTRATION IN GASES

BACKGROUND OF THE INVENTION

FIELD OF THE INVENTION

The invention relates to a device for measuring an oxygen content in gases. The measuring device has two configurations that enclose a gap between them and form a magnetic field. A sensor is held rotatably in the gap and can be deflected out of its position of rest as a function of the concentration of oxygen.

Such a device is used, for example, in chemical process technology.

Published, Non-Prosecuted German Patent Application DE 230 18 25 A discloses a method and a device which make use of the paramagnetic properties of oxygen in order to measure its concentration in a gas mixture. For this purpose, two magnets are disposed at a distance from one another in such a way that a gap of a defined size remains between them. Due to the magnetic field that forms in the gap, the oxygen is concentrated there. A measuring device with a sensor is disposed within the gap. The sensor is in the form of a dumbbell. It is held in such a way that it can be rotated about an axis that lies at its center of gravity. The sensor is moreover held in the gap in such a way that its longitudinal axis is oriented parallel to a longitudinal axis of the gap. The sensor is forced out of the gap when the oxygen concentration within the gap is increased in relation to the surroundings. The resulting deflection of the sensor is a measure of the oxygen concentration. With the aid of a mirror attached to the sensor and of a light balance disposed outside the gap, a highly accurate detection of the position of the sensor is possible. The sensor surface has disposed on it a coil that is led all around the edge of the sensor. With the aid of a current conducted through the coil, a restoring force can be generated, by which the sensor can be brought back into its position of rest again. The light balance determines when the position of rest has been reached. The magnitude of the current necessary for generating the restoring force is utilized in order to determine the oxygen concentration. There is a linear relation between the magnitude of the current and the oxygen concentration in the gap. A further measurement value that is used is the magnitude of the current that is necessary in order to bring the sensor out of the deflected position back into the position of rest when the gas mixture does not contain any oxygen.

The response times of the device are very long, since the inertia of the sensor is very high due to its structural configuration. Since the entire set-up of the device is large, the quantity of gas in the measurement chamber in which the device is disposed is also large. The exchange of the gas lasts for a correspondingly long time. Nor can it be sped up by a higher flow velocity, since this influences the deflection of the sensor and therefore leads to measurement errors.

SUMMARY OF THE INVENTION

It is accordingly an object of the invention to provide a device for measuring the oxygen concentration in gases which overcomes the above-mentioned disadvantages of the prior art devices of this general type, which has a minimized set-up and short response times.

With the foregoing and other objects in view there is provided, in accordance with the invention, a measuring device for determining the oxygen content in a gas. The measuring device has two devices enclosing a gap between them and forming a magnetic field. A frame is disposed in the gap and at least one sensor is held rotatably and moveably in the gap by the frame. The sensor can be deflected out of a position of rest in dependence on a concentration of the oxygen. The measuring device according to the invention is provided with the sensor that has small dimensions and which is held rotatably within the frame. The frame is disposed within the gap formed between the two configurations, by which a magnetic field can be generated in the gap. The sensor may be formed by a parallelepipedal body alone or by a parallelepipedal body to which a web-like structural element is fastened. Each of the parallelepipedal bodies is either hollow or solid. Preferably, the sensor is in the form of a dumbbell and is formed by two parallelepipedal bodies that are connected to one another via a web-shaped structural element. The web-shaped structural element is held rotatably in the frame centrally via two holding elements. The sensor, the frame and the holding elements are manufactured preferably from silicon. It is consequently possible to produce all the structural elements by etching techniques. Cost-effective mass production of the sensor becomes possible, using photolithography for structuring the etching mask.

At the same time, very narrow tolerances in the sensor properties, such as sensitivity and offset, can be achieved. To protect the silicon against corrosive gases, all the surfaces that are in contact with the gas atmosphere are coated with protective layers, such as silicon carbide, silicon nitride or silicon oxide.

The sensor is held by the resilient holding elements. The resilient holding elements are connected to the frame in such a way that they make it possible for the sensor to rotate about its mid-axis. The dimensions of the sensor are greatly reduced, as compared with known structures. The miniaturization of the sensor makes it possible to reduce the measurement gas volume. The exchange of the measurement gas can thereby take place more quickly, even when the flow velocity is reduced. This allows shorter response times and the reduction in the measurement errors, since disturbances due to the action of the flowing gases on the sensor are ruled out virtually completely. If the response times need to meet only reduced requirements, the application of current to the sensor may be dispensed with completely. Gas exchange then takes place by diffusion, without any adverse influence on the sensor.

By the decrease in the sensor height, the distance between the configurations generating the magnetic field can be reduced. As a result, the magnetic field strength in the gap is increased, and therefore a greater enrichment of oxygen within the gap is also achieved, so that the sensitivity of the sensor is appreciably improved. At least one conductor track is formed on the surface of the sensor. A current of variable magnitude can be conducted through the conductor track. With the aid of the current, a force is generated which is necessary for compensating the deflection of the sensor that the latter experiences in the magnetic field due to the concentration of oxygen. The conductor track is structured on the sensor by vapor deposition and etching methods.

In accordance with an added feature of the invention, at least one of the two boundary surfaces of the frame running parallel to one another has an orifice formed therein. The sensor has a region with a reflecting coating disposed thereon, and through the orifice electromagnetic radiation can be conducted onto the reflecting coating of the sensor.

In accordance with an additional feature of the invention, the sensor, the frame and the resilient holding elements are manufactured from silicon.

In accordance with another feature of the invention, a current source generating a current is provided. A conductor track is connected to the current source and is disposed on a surface of the sensor, and in that a restoring force of a defined magnitude acting on the sensor can be generated by the current conducted through the conductor track. In accordance with a further feature of the invention, the parallelepipedal bodies have a wall thickness and the sensor has a moment of inertia able to be set by the wall thickness of the parallelepipedic bodies.

In accordance with a further added feature of the invention, a deflection of the sensor can be limited to a defined value by geometric dimensions of the resilient holding elements.

In accordance with a concomitant feature of the invention, the sensor has a length of 2 to 15 mm, a width of 0.5 to 3 mm and a height of 0.1 to 2 mm, and the frame has an inner area of between 1.5 mm$^2$ and 50 mm$^2$.

Other features which are considered as characteristic for the invention are set forth in the appended claims.

Although the invention is illustrated and described herein as embodied in a device for measuring the oxygen concentration in gases, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
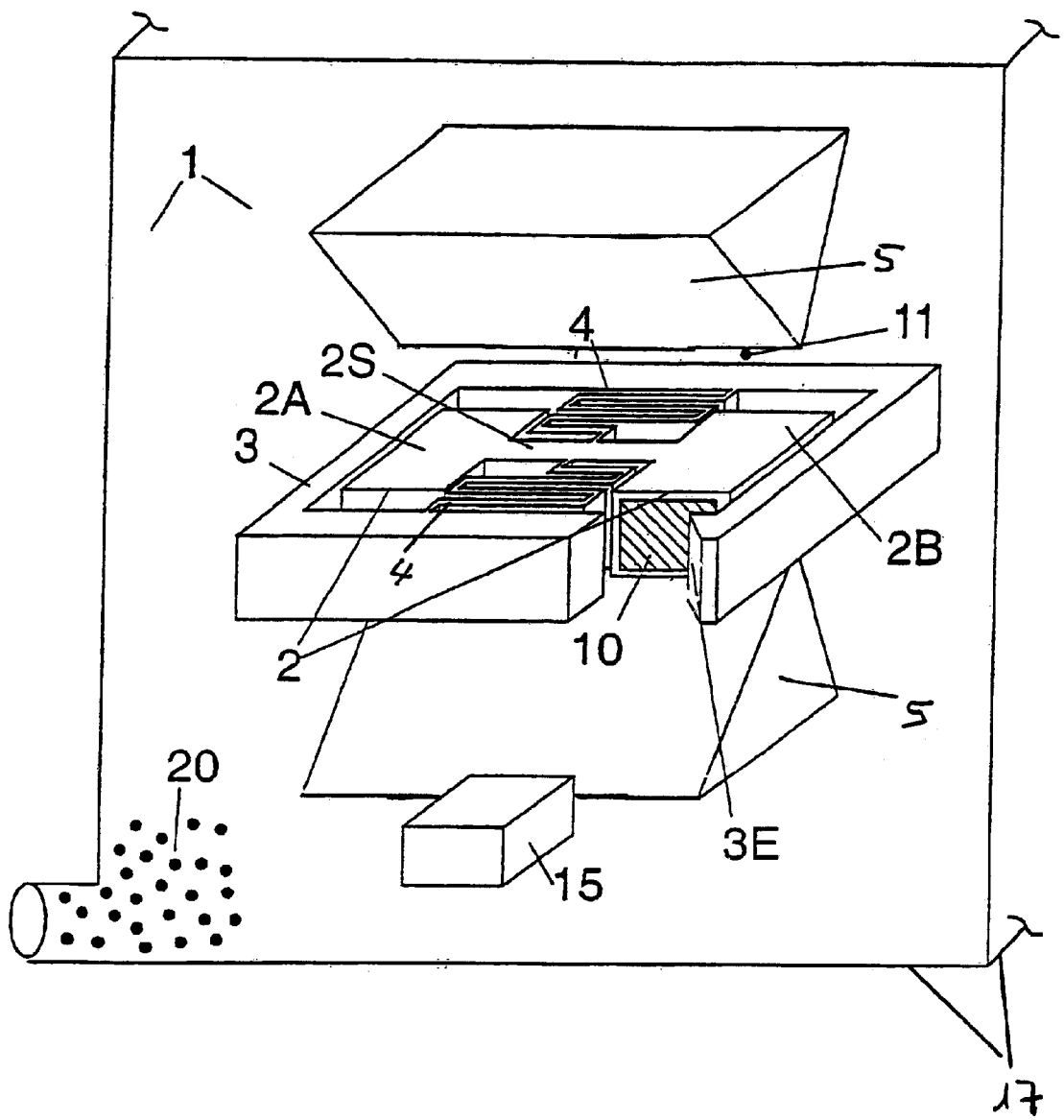
FIG. 1 is a diagrammatic, perspective view of a measuring device according to the invention.
Figure 3:
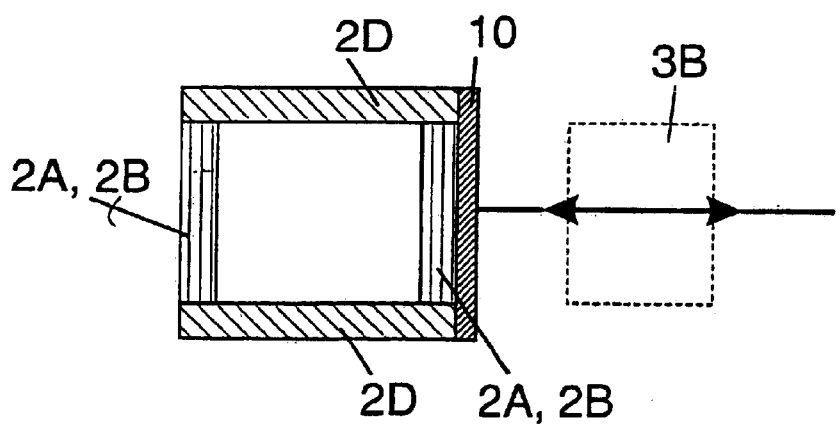
FIG. 3 is a sectional view of a part region of the sensor with incident and reflected radiation.

Referring now to the figures of the drawing in detail and first, particularly, to FIG. 1 thereof, there is shown a measuring device 1 that contains essentially a sensor 2, a frame 3, holding elements 4 and two configurations 5 for generating a magnetic field. The sensor 2, the frame 3 and the holding elements 4 are manufactured preferably from silicon or from a material with comparable properties. It is consequently possible to employ the microtechniques, bonding and etching methods already belonging to the prior art in order to produce the measuring device 1. To protect the silicon against corrosive gases, all the surfaces that are in contact with the gas atmosphere are coated with protective layers, such as silicon carbide, silicon nitride or silicon oxide. The sensor 2 is configured preferably, with a length of 2 to 15 mm, a width of 0.5 to 3 mm and a height of 0.1 to 2 mm. The sensor 2 is formed by two parallelepipedal bodies 2A and 2B of equal size that are connected to one another via a web-shaped structural element 2S. The height of the parallelepipedal bodies 2A and 2B corresponds to the height of the sensor 2. The boundary surfaces of the bodies 2A and 2B are square and have a side length of 1 mm. However, the side surfaces may also be of rectangular configuration. The two bodies 2A and 2B are of equal size and are both hollow on the inside. The body 2A, 2B is illustrated in vertical section in FIG. 3. A wall thicknesses of the bodies 2A and 2B are 0.1 mm. The wall thicknesses may, however, be varied, specifically in such a way that the sensor 2 has the moment of inertia desired in each case. Should the bodies 2A and 2B be hollow on the inside, they are closed to the top and bottom in each case by a cover 2D, as is illustrated in FIG. 3. The covers 2D may be manufactured from glass or silicon and are connected to the body 2A, 2B with the aid of a bonding method.

The two bodies 2A and 2B are connected to one another via the web-shaped structural element 2S, in such a way that the sensor 2 formed from them is in the form of a dumbbell. The length of the web-shaped structural element 2S is dimensioned such that the sensor 2 has the overall length specified above. A width of the web-shaped structural element 2S is 0.2 mm in the exemplary embodiment illustrated here. Its thickness corresponds approximately to the height of the bodies 2A and 2B without the covers 2D.

Figure 2:
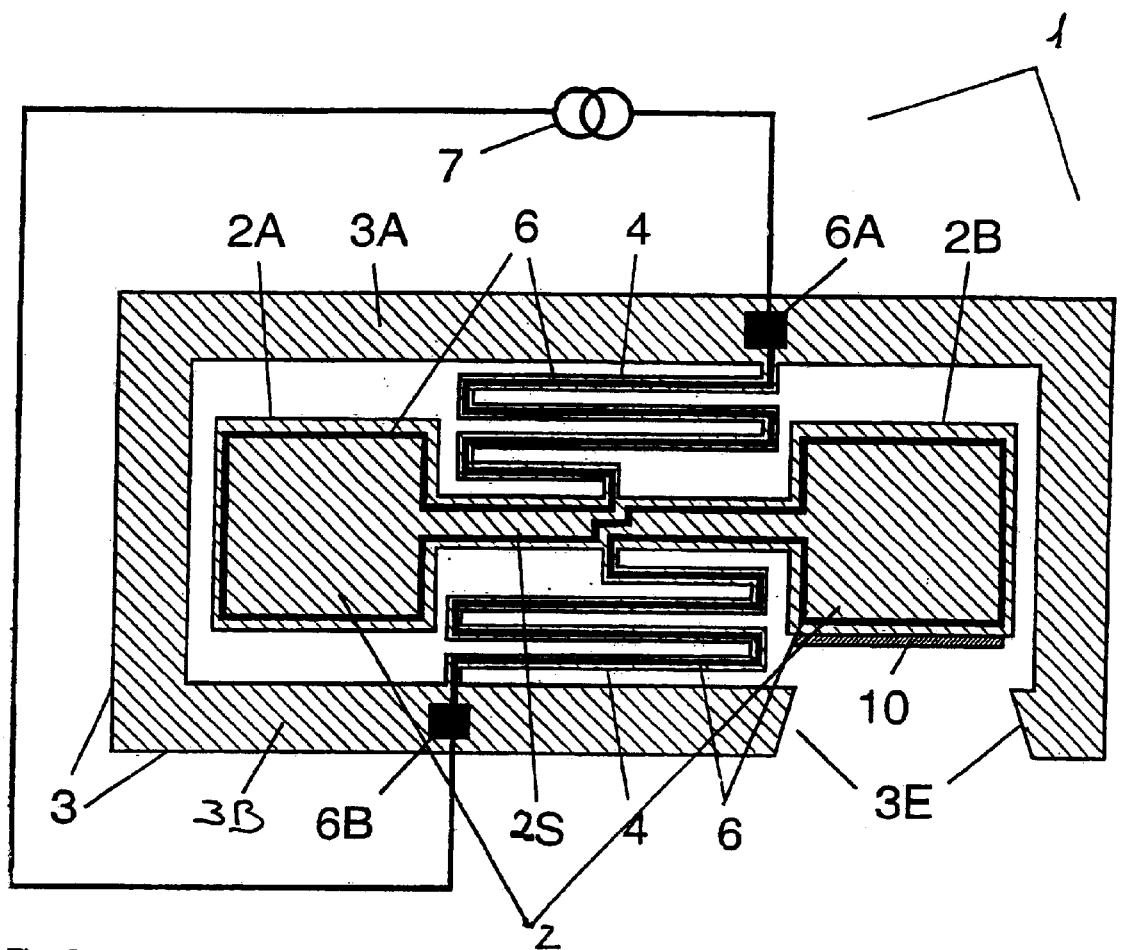
FIG. 2 is top plan view of a sensor of the measuring device shown in FIG. 1.

As shown in FIG. 2, the sensor 2 thus formed is disposed inside the frame 3. The dimensions of the frame 3 are selected such that the sensor 2 can rotate about an axis that passes perpendicularly through its center of gravity. The deflection of the sensor 2 should amount to at least 30°0. The height of the frame 3 is slightly smaller than the height of the sensor 2. The sensor 2 is fastened to two boundary surfaces 3A, 3B of the frame 3, which run parallel to the longitudinal axis of the web-shaped structural element 2S, in each case by a resilient holding element 4. The two holding elements 4 are configured as bands that are both disposed in a meander-like manner. Alternatively, the meander-like configuration of the bands 4 may be dispensed with if a sufficient restoring force can also be established by non-illustrated leaf spring-like bands of a reduced width. In each case one end of each holding element 4 is connected fixedly to the boundary surface 3A, 3B of the frame 3, while the second end of each holding element 4 is connected to the web-shaped structural element 2S. The dimensions of the holding elements 4 are always coordinated with the mass of the sensor 2. Instead of the bands, other resilient holding elements 4, which allow an appropriate rotation of the sensor within the frame 3, may also be used in order to fasten the sensor 2.

As may also be gathered from FIG. 2, a surface of the sensor 2 has formed on it an electrical conductor track 6 that is produced with the aid of one of the known thin-film methods. The conductor track 6 is manufactured preferably by vapor deposition, sputtering or an electroplating method from a metallic material in the form of Au, Ag, Cu, Pt or Al.

Alternatively, it may also be formed by the diffusion of donors or acceptors into the silicon. In each case an electrical connecting element 6A, 6B of the conductor track 6 is disposed on the top side of the boundary surface 3A, 3B of the frame 3. The conductor track 6 is led from there over the surface of one of the resilient holding elements 4 as far as the surface of the sensor 2 and along the web-shaped structural element 2S as far as the first body 2A. The conductor track 6 is then led along the outer edge of the body 2A back as far as the web-shaped structural element 2S and over this as far as the second body 2B. It is then led back along the edge of the body 2B to the web-shaped structural element 2S and over the second holding element 4 to the second electrical connecting element 6B. The two connecting elements 6A and 6B may be connected to a current source 7.

Alternatively, the conductor track 6 may also be formed on the surface of the sensor 2 in such a way that the current flowing in the conductor track runs around the two bodies 2A, 2B in the same direction. This necessitates an intersection point of the conductor track 6 at which the intersecting portions of the conductor track (which are not illustrated here) are then electrically insulated from one another.

As may be seen from FIG. 1, in the exemplary embodiment illustrated here one boundary surface 3B of the frame 3, the boundary surface being oriented parallel to the longitudinal axis of the sensor 2, is provided with an orifice 3E in the region of one body 2B. The body 2B has a coating 10 on its side surface that faces the boundary surface 3B. The coating 10 is configured to reflect electromagnetic radiation of a specific frequency, preferably light in the visible range. A device 15 is installed outside the frame 3. Electromagnetic radiation is conducted from the device 15 onto the coating 10. The electromagnetic radiation 16 reflected from there is also received by the device 15 again, as illustrated in FIG. 3. In the event of a change in position of the sensor 2, the signal received by the device 15 changes. It is consequently possible to determine the position of the sensor 2 with a high degree of accuracy. Alternatively to a reflecting coating, the natural reflection of the material from which the sensor 2 is manufactured may also be utilized. This is the case, for example, when the sensor 2 is produced from silicon and visible electromagnetic radiation 16 is emitted by the device 15.

Figure 4:
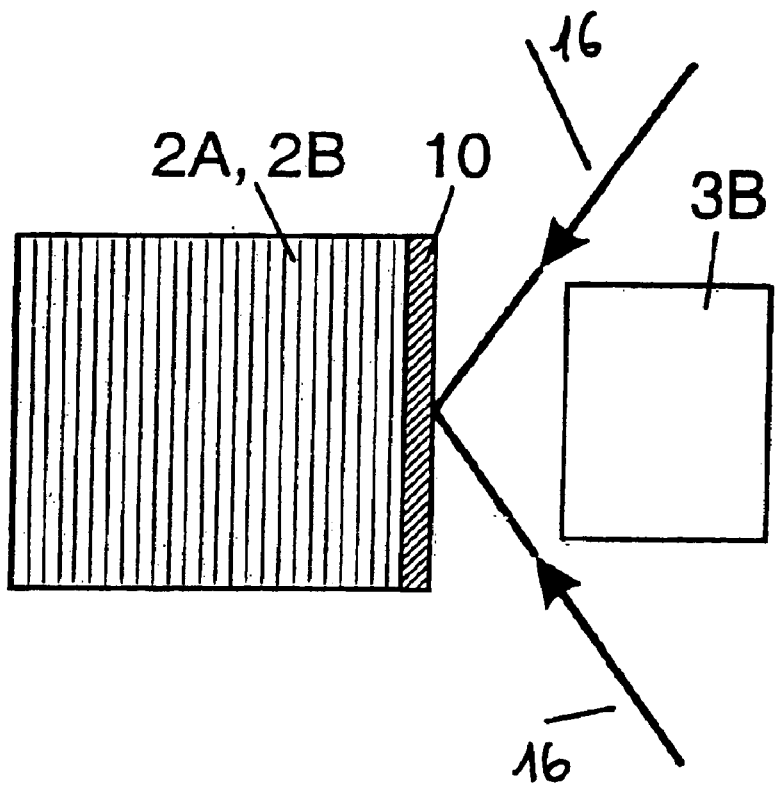
FIG. 4 is a sectional view of a variant of the part region illustrated in FIG. 3.
Figure 5:
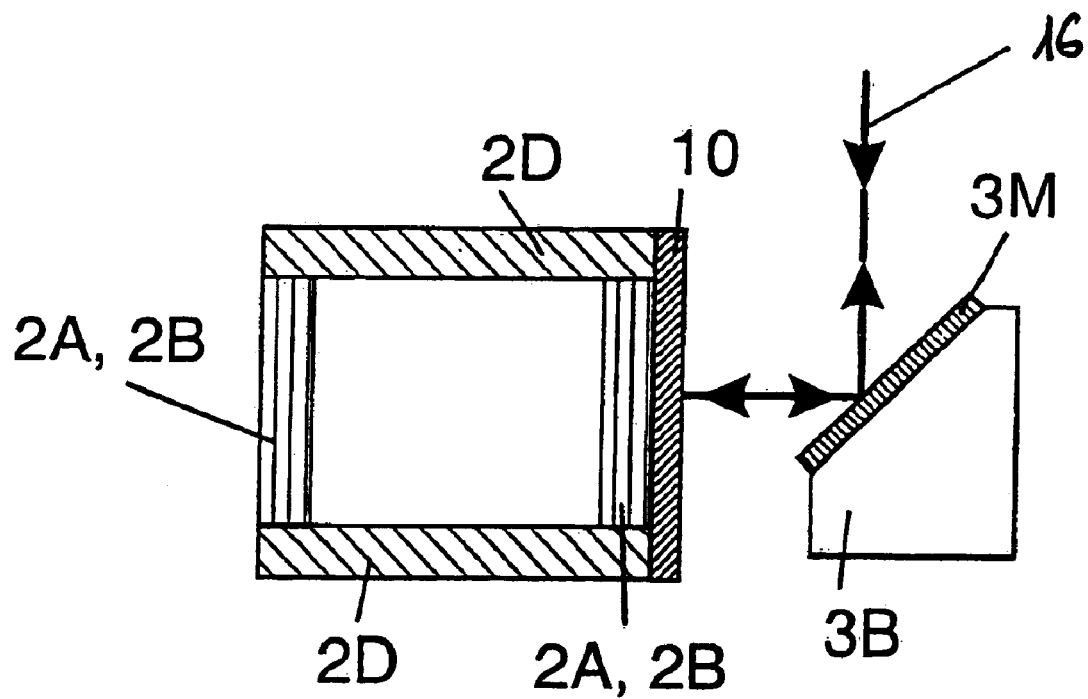
FIG. 5 is a sectional view of a further variant of the part region illustrated in FIG. 3.

Instead of the coating 10, a non-illustrated mirror may also be formed with the aid of a concavely or convexly shaped lateral surface of the body 2B. In favor of increased mechanical stability of the frame 3, the orifice 3E may be dispensed with if the electromagnetic radiation 16 is guided onto the coating 10 obliquely from above or below, as shown in FIG. 4. The radiation 16 may also be guided onto the reflecting side surface of the body 2B via a deviating mirror 3M. The deviating mirror 3M is disposed on the inside of the frame 3, opposite the reflecting side surface of the body 2B, as is illustrated in FIG. 5.

As shown in FIG. 1, the frame 3 together with the sensor 2 located in it is positioned in a gap 11 between the two configurations 5 that are disposed at a distance from one another. In the exemplary embodiment illustrated here, the two configurations 5 are formed in each case by a permanent magnet 5. The two permanent magnets 5 both have a V-shaped cross section in the exemplary embodiment illustrated here.

Alternatively, the cross section may also be rectangular. However, to form the magnetic field, electromagnets may also be used instead of the permanent magnets 5.

The two permanent magnets 5 are disposed in such a way that their longitudinal axes run parallel to one another, and, in the case of a V-shaped cross section, they point toward one another in a sweptback manner. The frame 3 is positioned in such a way that the longitudinal axis of the sensor 2 is oriented parallel to the longitudinal axes of the permanent magnets 5. The distance between the two configurations 5 is determined by the height of the sensor 2. The measurement device 1 and the two configurations 5 are disposed in a measuring chamber 17. A gas 20 that is to be investigated and an oxygen fraction of which is to be determined is introduced into the measuring chamber 17. If the gas 20 contains oxygen, the latter is concentrated in the gap 11 on account of its paramagnetic property. Due to the higher gas density in the gap 11, a force acts on the sensor 2 and endeavors to force the sensor 2 out of the gap 11. The sensor 2 is rotated about its suspension point as a function of the magnitude of the force. The deflection is detected by the device 15. With the aid of the current source 7, which is connected to the two electrical connecting elements 6A and 6B of the conductor track 6, what is achieved is that a current generating a counterforce flows in the conductor track 6. With the aid of a correspondingly high current, the sensor 2 can be moved back into its position of rest again. By an appropriate setting of the geometric dimensions of the resilient holding elements 4, what can be achieved is that the force which has to be applied in order to guide the sensor 2 back into its position of rest again even when there is a maximum quantity of oxygen in the gap 11 does not exceed a defined value. The device 15 detects that the position of rest has been reached. The magnitude of the current is used for determining the oxygen fraction in the gas 20. What is used as a reference magnitude is the magnitude of a current that is necessary to bring the sensor 2 back into its position of rest when there is no oxygen concentrating in the gap 11. This purpose is served by the fact that, due to assembly tolerances, the sensor assumes a position of rest that is not identical to the neutral position of the device 15. The magnitude of the current necessary for returning the sensor 2 into the neutral position of the device may be used as reference magnitude. Likewise, in order to determine a reference magnitude, use may be made of the fact that the material employed for manufacturing the sensor 2 is, where appropriate, diamagnetic or paramagnetic, so that the sensor 2 experiences a direct force in the magnetic field.

As illustrated in FIG. 4, the bodies 2A and 2B may also be made solid. In this case, the covers 2D may be dispensed with. In this embodiment, too, the mass and therefore also the size of the bodies 2A and 2B are dimensioned such that the sensor 2 has the desired moment of inertia.

In a simplified embodiment of the measuring device, the sensor 2 may also be configured in such a way that it has only one body 2A, 2B that is connected (not illustrated here) to the web-shaped structural element 2S. The free end of the web-shaped structural element 2S is then fastened to the frame 3 via one or two holding elements 4, as already described above.

Likewise (not illustrated here), the sensor 2 may also be formed of only one parallelepipedal body which is made solid or hollow and is held rotatably in the frame 3 centrally by the resilient holding elements 4.

We claim:

1. A measuring device for determining an oxygen content in a gas, comprising:
   a frame disposed in a magnetic field; and
   a sensor held pivotally by said frame for rotation relative to said frame, said sensor to be deflected out of a position of rest in dependence on a concentration of the oxygen content in the gas outside of said sensor.

2. The measuring device according to claim 1,
   wherein said sensor has at least one parellelepipedal body selected from the group consisting of hollow parallelipipedal bodies and solid parallelepipedal bodies;
   including a web-shaped structural element connected to said parallelepipedal body; and
   at least one resilient holding element fastened to said frame and to said web-shaped structural element allowing said sensor to be held pivotally within said frame.

3. The measuring device according to claim 1,
   wherein said sensor is a parallelepipedal body selected from the group consisting of hollow parallelepipedal bodies and solid parallelepipedal bodies; and including at least one resilient holding element for holding said parallelepipedal body pivotally within said frames, said resilient holding element connected to said frame and to said sensor.

4. The measuring device according to claim 1, wherein said sensor has two parallelepipedal bodies selected from the group consisting of hollow parallelepipedal bodies and solid parallelepipedal bodies, and a web-shaped structure element connecting said two parallelepipedal bodies to one another, said web-shaped structural element having a length dimensioned such that said sensor is rotatable within said frame; and including resilient holding elements connected to said frame and said web-shaped structural element such that said web-shaped structural element is held centrally, in each case via said resilient holding elements, on two boundary surfaces of said frame which are oriented parallel to one another.

5. The measuring device according to claim 4, wherein at least one of said two boundary surfaces of said frame running parallel to one another has an orifice formed therein, said sensor having a region with a reflecting coating disposed thereon, and through said orifice electromagnetic radiation can be conducted onto said reflecting coating of said sensor.

6. The measuring device according to claim 4, wherein said sensor, said frame and said resilient holding elements are manufactured from silicon.

7. The measuring device according to claim 4, wherein said parallelepipedal bodies have a wall thickness and said sensor has a moment of inertia able to be set by said wall thickness of said parallelepipedal bodies.

8. The measuring device according to claim 4, wherein a deflection of said sensor can be limited to a defined value by geometric dimensions of said resilient holding elements.

9. The measuring device according to claim 1, including:

a current source generating a current; and a conductor track connected to said current source and disposed on a surface of said sensor, and in that a restoring force of a defined magnitude acting on said sensor can be generated by the current conducted through said conductor track.

10. The measuring device according to claim 1, wherein said sensor has a length of 2 to 15 mm, a width of 0.5 to 3 mm, and a height of 0.1 to 2 mm, and said frame has an inner area of between 1.5 mm$^2$ and 50 mm$^2$.

11. The measuring device according to claim 1, further comprising two devices forming said magnetic field.

12. The measuring device according to claim 1, wherein a deflection of said sensor can be limited to a defined value by geometric dimensions of said resilient holding elements.

13. A measuring device for determining an oxygen content in a gas, comprising:

two devices enclosing a gap between them and forming a magnetic field;

a frame disposed in said gap, said frame having an inner area of between 1.5 mm$^2$ and 50 mm$^2$;

a sensor held rotatably and moveably in said gap by said frame, said sensor being able to be deflected out of a position of rest in dependence on a concentration of the oxygen, said at least one sensor having a length 2 mm to 15 mm, a width of 0.5 mm to 3 mm, a height 0.1 mm, to 2 mm and being provided with two parallelepipedal bodies selected from the group consisting of hollow parallelepipedal bodies having a wall thickness and solid parallelepipedal bodies having a wall thickness, and said sensor has a moment of inertia set by said wall thickness of said parallelepipedal bodies;

a web-shaped structure element connecting said two parallelepipedal bodies to one another and having a length dimensioned that said sensor is rotatable within said frame;

resilient holding elements connecting said frame and said web-shaped structural element such that said web-shaped structural element is held centrally by said resilient holding elements on two boundary surfaces of said frame oriented parallel to one another;

said sensor having a region with a reflecting coating disposed thereon and at least one of said two boundary surfaces of said frame running parallel to one another having an orifice formed therein through which electromagnetic radiation is conducted onto said reflecting coating of said sensor;

a current source; and a conductor track disposed on a surface of said sensor and connected to said current source providing a current generating a restoring force of a defined magnitude acting on said sensor.

14. The measuring device according to claim 1, wherein said sensor, said frame, and said resilient holding elements are manufactured from silicon.

* * * * *